United States Patent
Dvorkin et al.

(10) Patent No.: US 8,155,377 B2
(45) Date of Patent: Apr. 10, 2012

(54) METHOD FOR DETERMINING ROCK PHYSICS RELATIONSHIPS USING COMPUTER TOMOGRAPHIC IMAGES THEREOF

(75) Inventors: Jack Dvorkin, Redwood City, CA (US); Naum Derzhi, Sugarland, TX (US); Meghan Armbruster, Houston, TX (US); Qian Fang, Houston, TX (US); Zbigniew Wojcik, Houston, TX (US)

(73) Assignee: Ingrain, Inc., Houston, TX (US)

( * ) Notice: Subject to any disclaimer, the term of this patent is extended or adjusted under 35 U.S.C. 154(b) by 588 days.

(21) Appl. No.: 12/276,430

(22) Filed: Nov. 24, 2008

(65) Prior Publication Data

US 2010/0128932 A1 May 27, 2010

(51) Int. Cl.
*G06K 9/00* (2006.01)
*E21B 10/02* (2006.01)

(52) U.S. Cl. .................... 382/100; 382/154; 175/249

(58) Field of Classification Search .................. 382/100, 382/103, 106, 107, 108, 109, 128–131, 154, 382/162, 165, 168, 170, 173, 181, 189–194, 382/199, 221, 224, 232, 254, 274, 276, 285–292, 382/294, 305, 312; 166/298; 367/14; 175/17; 702/16; 324/303; 378/53, 21
See application file for complete search history.

(56) References Cited

U.S. PATENT DOCUMENTS

| | | | | |
|---|---|---|---|---|
| 5,335,724 A | * | 8/1994 | Venditto et al. | 166/298 |
| 5,877,995 A | * | 3/1999 | Thompson et al. | 367/14 |
| 6,516,080 B1 | * | 2/2003 | Nur | 382/109 |
| 6,742,603 B2 | * | 6/2004 | Polizzotti et al. | 175/17 |
| 6,807,487 B2 | * | 10/2004 | Khan | 702/16 |
| 6,933,719 B2 | * | 8/2005 | Thomann et al. | 324/303 |
| 7,869,565 B2 | * | 1/2011 | Wood et al. | 378/53 |

FOREIGN PATENT DOCUMENTS

WO 2005108965 A1 11/2005

OTHER PUBLICATIONS

Bugani et al, "Investigating morpholgical changes in treated vs. untreated stone building materials by x-ray micro-CT", Anal Boiannal. Chem (2008); 391.1343-1350.

Felipuissi et al, Measuring Statistical Geometric Properties of Tomographic Images of Soils, IEEE Trnasactions on Instrumentation and Measurement v. 57, No. 11.

E. Galluci et al., "3D experimental investogation of the microstructure of cement pastes . . .", Cement and Concrete Research 37 (2007) 360-368.

De Graef et al, "A sensititvity study for the visualization of bacterial weathering of concrete and stone . . ." Science of the Total Environment 341 (2005) 173-183.

(Continued)

*Primary Examiner* — Seyed Azarian
(74) *Attorney, Agent, or Firm* — Kilyk & Bowersox, P.L.L.C.

(57) ABSTRACT

A method for estimating a relationship between physical properties of a porous material from a sample thereof includes making a three dimensional tomographic image of the sample of the material. The image is segmented into pixels each representing pore space or rock grains. The image is divided into sub-volumes. A porosity is estimated for each sub-volume. At least one petrophysical parameter is modeled from the image of each sub-volume. A relationship between the porosity and the at least one modeled petrophysical parameter is determined by, e.g., a best-fit statistical method. The relationship and the modeled petrophysical parameter for each sub-volume are stored in a computer or displayed.

11 Claims, 3 Drawing Sheets

OTHER PUBLICATIONS

Jones et al., "Chracterization of methane hydrate host sediments using synchrotron-computer miccrtotomography, "J. Petr. Sci. and Eng. 56 (2007) 136-145.

Youssef et al., "High Resolution CT and Pore-Network Models to Assess Petrophysical Properties of Homogeneous and Heterogeneous Carbonates," Society of Petroleum Engineers/EAGE Reservoir Characterization and Simulation Conference, SPE No. 111427, Oct. 29, 2007, pp. 1-12 (12 pages).

Knackstedt et al., "Digital Core Laboratory: Properties of reservoir core derived from 3D images," Society of Petroleum Engineers Asia Pacific Conference on Integrated Modelling For Asset Management, SPE No. 87009, Mar. 29, 2004, pp. 1-14 (14 pages).

Adams et al., "Seeded Region Growing," IEEE Transactions on Pattern Analysis and Machine Intelligence, vol. 16, No. 6, Jun. 1994, pp. 641-647 (7 pages).

Sakellariou et al., "Developing A Virtual Materials Laboratory," Materials Today, vol. 10, No. 12, Dec. 2007, pp. 44-51 (8 pages).

Sandberg, "Methods For Image Segmentation in Cellular Tomography," Methods in Cell Biology, vol. 79, Jan. 1, 2007, pp. 769-798 (32 pages).

Parker, "Gray Level Thresholding in Badly Illuminated Images," IEEE Transactions on Pattern Analysis and Machine Intelligence, vol. 13, No. 8, Aug. 1, 1991, pp. 813-819 (7 pages).

Oh et al., "Image Thresholding by Indicator Kriging," IEEE Transactions on Pattern Analysis and Machine Intelligence, vol. 21, No. 7, Jul. 1999, pp. 590-602 (13 pages).

International Search Report and Written Opinion of the International Searching Authority issued in corresponding International Patent Application No. PCT/US2009/065401 dated May 4, 2011 (13 pages).

Arns et al., "Computation of linear elastic properties from microtomographic images: Methodology and agreement between theory and experiment," Geophysics, vol. 67, No. 5, Sep.-Oct. 2002, pp. 1396-1405.

Auzerais et al., "Transport in sandstone: A study based on three dimensional microtomography,"Geophysical Research Letters, vol. 23, No. 7, Apr. 1, 1996, pp. 705-708.

Fredrich et al., "Predicting macroscopic transport properties using microscopic image data,"Journal of Geophysical Research, vol. 111, 2006, 14 pages.

Oh et al., "Image Thresholding by Indicator Kriging," IEEE Transactions on Pattern Analysis and Machine Intelligence, vol. 21, No. 7, Jul. 1999, pp. 590-601 (13 pages).

Rothman et al., "Single-phase flow," Section 13.3, Lattice-Gas Cellular Automata, Simple models of complex hydrodynamics, published 1997, pp. 155-157 (5 pages).

* cited by examiner

US 8,155,377 B2

METHOD FOR DETERMINING ROCK PHYSICS RELATIONSHIPS USING COMPUTER TOMOGRAPHIC IMAGES THEREOF

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates generally to the field of estimating material properties of porous media. More specifically, the invention relates to methods for estimating such properties using computer tomographic (CT) images of porous media such as subsurface rock formation.

2. Background Art

Estimating material properties such as effective elastic and shear moduli, electrical resistivity and fluid transport properties of porous media, for example, mobility of hydrocarbon in subsurface rock formations, has substantial economic significance. Methods known in the art for identifying the existence of subsurface hydrocarbon reservoirs, including seismic surveying and well log analysis, need to be supplemented with reliable methods for estimating how fluids disposed in the pore spaces of reservoir rock formations will flow over time in order to characterize the economic value of such reservoir rock formations.

One method known in the art for estimating fluid transport properties is described in U.S. Pat. No. 6,516,080 issued to Nur. The method described in the Nur patent includes preparing a "thin section" from a specimen of rock formation. The preparation typically includes filling the pore spaces with a dyed epoxy resin. A color micrograph of the section is digitized and converted to an n-ary index image, for example a binary index image. Statistical functions are derived from the two-dimensional image and such functions are used to generate three-dimensional representations of the rock formation. Boundaries can be unconditional or conditioned to the two-dimensional n-ary index image. Desired physical property values are estimated by performing numerical simulations on the three-dimensional representations. For example, permeability is estimated by using a Lattice-Boltzmann flow simulation. Typically, multiple, equiprobable three-dimensional representations are generated for each n-ary index image, and the multiple estimated physical property values are averaged to provide a result.

In performing the method described in the Nur patent, it is necessary to obtain samples of the rock formation and to prepare, as explained above, a section to digitize as a color image. Economic considerations make it desirable to obtain input to fluid transport analysis more quickly than can be obtained using prepared sections. Recently, devices for generating CT images of samples such as drill cuttings have become available. Such CT image generating devices (CT scanners) typically produce three-dimensional gray scale images of the samples analyzed in the scanner. Such gray scale images can be used, for example, essentially contemporaneously as drill cuttings are generated during the drilling of a wellbore through subsurface rock formations.

Using images of samples of rock formations it is possible to obtain estimates of petrophysical parameters of the imaged rock sample, for example, porosity, permeability, shear and bulk moduli, and formation resistivity factor. The foregoing parameters are typically distributed within ranges in each rock formation, and there may be determinable relationships between such parameters such that determining one parameter value can enable determining one or more of the other parameters. One way to establish such relationship is to determine one or more rock physics transforms. A rock physics transform is a mathematical formula or algorithm that relates one property of a rock formation to another. Such transforms can be based on an idealized mathematical model of rock, such as the differential effective medium that models rock as a solid with ideal-shape inclusions or the Hertz-Mindlin model that models rock as a composite made of perfect elastic spheres. Such transforms can also be based on a sufficient number of experimental data (e.g., well log measurements or laboratory measurements) using a statistically fit expression that approximates such data. An example of the latter is the Raymer transform between porosity $\phi$ and the compressional wave (P-wave) velocity of the rock ($V_p$). The transform is the expression $V_p=(1-\phi)^2 V_{ps}+\phi V_{pf}$, where $V_{ps}$ is the P-wave velocity in the mineral (matrix or solid) phase of the rock (e.g., quartz) and $V_{pf}$ is the P-wave velocity in the pore fluid (e.g., water). The elastic (compressional) wave velocity is directly related to the bulk K and shear G moduli by the expression $V_p=\sqrt{(K+4G/3)\rho}$, where $\rho$ is the bulk density of the rock. The foregoing moduli can be obtained by laboratory measurement, and can also be obtained by calculations made from an image of a rock sample. Another example is the relationship between the absolute permeability k and the porosity $\phi$ of a rock formation called the Kozeny-Carman relation, represented by the expression $k=d^2\phi^3/[72\tau^2(1-\phi)^2]$, where d is the mean rock grain size and $\tau$ is the pore tortuosity (typically represented by a number between 1 and 5). Yet another example is Humble's relationship between the electrical resistivity formation factor F and the porosity $\phi$, represented by the expression $F=a/\phi^m$, where a and m are constants that are determined experimentally. As in the P-wave velocity example, the parameters that enter these two equations, one for permeability and the other for the formation factor, can be obtained by laboratory measurement and also by calculations based on an image of a rock sample. Instead of using the permeability (k) and formation factor (F) equation examples above, one may conduct a large number of laboratory tests on samples that represent the formation under examination. Alternatively, such data can be obtained by digital calculations on a digitally imaged rock sample.

Obtaining and calibrating rock physics transforms using physical samples and using measurements made on actual rock samples requires extensive laboratory and/or well measurements. There exists a need to use images such as the foregoing CT scan images to estimate relationships between formation parameters without the need for extensive laboratory or well measurements.

SUMMARY OF THE INVENTION

A method according to one aspect of the invention for estimating a relationship between physical properties of a porous material from a sample thereof includes making a three dimensional tomographic image of the sample of the material. The image is segmented into pixels each representing pore space or rock grains. The image is divided into sub-volumes. A porosity is estimated for each sub-volume from the image thereof. At least one petrophysical parameter is modeled from the image of each sub-volume. A relationship between the porosity and the at least one modeled petrophysical parameter is determined. The relationship and the modeled petrophysical parameter for each sub-volume are stored in a computer or displayed.

Other aspects and advantages of the invention will be apparent from the following description and the appended claims.

DETAILED DESCRIPTION

The description of this invention is made with reference to using drill cuttings obtained during the drilling of a wellbore through subsurface formations. It should be clearly understood that drill cuttings is only one example of samples of rock formation that may be used with the present invention. Any other source of a rock formation sample, e.g., whole cores, sidewall cores, outcrop quarrying, etc. may provide suitable samples for analysis using methods according to the invention. Consequently, the invention is not limited in scope to analysis of drill cuttings.

Figure 1:
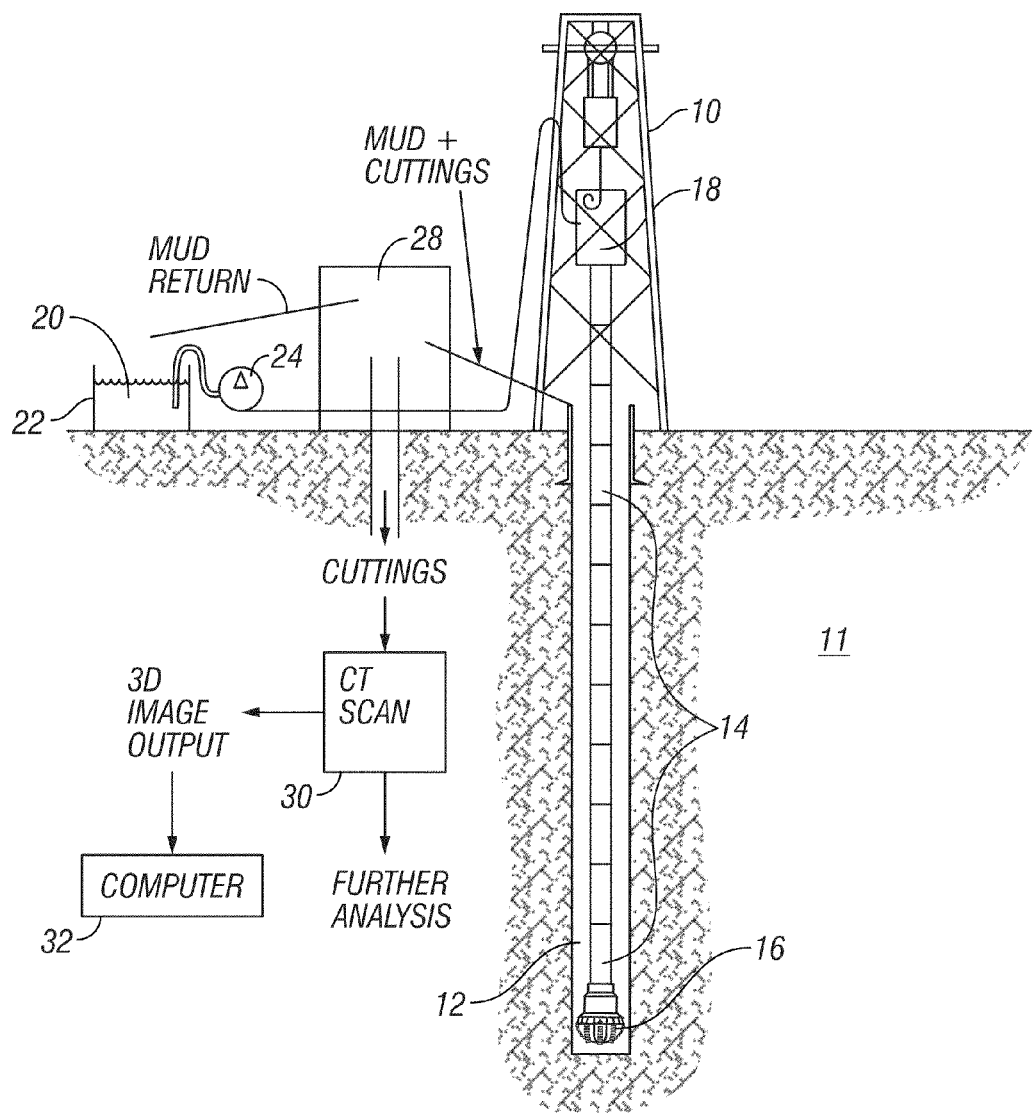
FIG. 1 shows an example of obtaining cuttings during drilling of a wellbore and analysis thereof during the drilling.

An example of drilling a wellbore to obtain samples of rock formations for evaluation by examples of a method according to the invention will be explained with reference to FIG. 1. A drilling unit or "rig" 10 is disposed at the Earth's surface. The rig 10 includes lifting equipment (not shown separately) for raising and lowering one of several types of device used to rotate a drill string 14. The device, shown at 18 in the present example may be a top drive, although the use of a tope drive is not a limit on the scope of the invention. The drill string 14 is assembled by threadedly coupling segments of drill pipe end to end. A drill bit 16 is disposed at the lower end of the drill string 14 and cuts through subsurface rock formations 11 to form a wellbore 12. During the drilling of the wellbore 12, the rig 10 is operated to cause some of the axial load (weight) of the drill string 14 to be applied to the drill bit 16. The top drive 18 rotates the drill string 14 and the drill bit 16 at the lower end thereof. The combination of axial load and rotation causes the drill bit 16 to cut through the formations 11.

The rig 10 includes a tank or pit 22 having drilling fluid ("mud") 20 stored therein. A pump 24 lifts the mud 20 and discharges it through suitable flow lines 26 so that the mud 20 passes through an internal passage in the drill string 14, whereupon it is discharged through suitable orifices or courses in the drill bit 16. The discharged mud 20 cools and lubricates the drill bit 16 and lifts the cuttings generated by the bit 16 to the Earth's surface. The cuttings and mud thus lifted enter separation and cleaning devices, shown generally at 28 and including, for example, devices known as "degassers" and "shale shakers" to remove the cuttings and contamination from the mud 20. The mud after such cleaning is returned to the pit 22 for subsequent use in drilling the wellbore 12.

In the present example, the cuttings removed from the separation and cleaning device 28 may be transported to a computer tomographic ("CT") scanner 30, which may use x-rays for analysis of internal structure of the cuttings, for generation of three dimensional (3D) images of the cuttings. The images so generated may be in numerical form and their content will be further explained below. After CT scanning, the cuttings may be saved for further analysis or may be suitably discarded. An example of a suitable CT scanner for making images usable with methods according to the invention is sold under model designation MicroXCT Series 3D tomographic x-ray transmission microscope by Xradia, Inc., 5052 Commercial Circle, Concord, Calif. 94520.

In some examples, an analysis of the cuttings from the CT scan images may provide, substantially in real time during the drilling of the wellbore, an estimate of certain properties of the subsurface formations being drilled, for example fluid mobility of one or more constituent fluids in the pore spaces of the rock formations 11. In the present example, images generated by the CT scanner 30 may be transferred to a computer 32 having program instructions for carrying out image analysis and subsequent formation property modeling as described below.

It should also be understood that drill cuttings are only one type of rock sample that may be analyzed according to the invention. In other examples, the drill bit 16 may be an annular type configured to drill whole cores of the rock formations 11. In other examples, percussion sidewall core samples may be obtained during drilling or when the drill string 14 is withdrawn from the wellbore 12 such as for "wireline" well evaluation techniques. Accordingly, the scope of the invention is not limited to analysis of drill cuttings. As explained above, the invention is also not limited to use with rock samples obtained from a wellbore drilled through subsurface rock formations.

CT scan imaging of a porous material sample (e.g., a sample of rock formation) is used in the invention to produce a numerical object that represents the material sample digitally in the computer 32 for subsequent numerical simulations of various physical processes, such as viscous fluid flow (for permeability estimation); stress loading (for the effective elastic moduli); electrical current flow (for resistivity); and pore size distribution for nuclear magnetic resonance relaxation time properties, including distribution of relaxation time. In some examples, such analysis can be performed while drilling operations are underway, substantially in real time.

The CT scan image produced by the CT scanner 30 may be a 3D numerical object consisting of a plurality of 2D sections of the imaged sample. Each 2D section consists of a grid of values each corresponding to a small region of space defined within the plane of the grid. Each such small region of space is referred to as a "pixel" and has assigned thereto a number representing the image darkness (or for example the density of the material) determined by the CT scan procedure. The value ascribed to each pixel of the 2D sections is typically an integer that may vary between zero and 255 where 0 is, e.g., pure white, and 255 is pure black. Such integer is typically referred to as a "gray scale" value. 0 to 255 is associated with eight digital bits in a digital word representing the gray scale value in each pixel. Other gray scale ranges may be associated with longer or shorter digital words in other implementations, and the range of 0 to 255 is not intended to limit the scope of the invention. For the purpose of simulating a physical process using such a numerical object (the gray scale), however, the numerical object is preferably processed so that all the pixels allocated to the void space in the rock formation (pore space) are represented by a common numerical value, e.g., by only 255s, and all the pixels associated with the rock matrix (or rock grains) are represented by a different numerical value, for example, zeroes. The foregoing process is called image segmentation. Subsequently, the resulting numerical object can be normalized so that the pore spaces are represented by, for example, ones and the rock grains are represented by zeroes. The foregoing may be described as converting the image into a binary index. In other examples, the image may be converted into an index having any selected number, n, of indices. It has been determined that sufficiently accurate modeling of some rock petrophysical parameters or properties, e.g. permeability, may be obtained using a binary index, in which one value represents pore space and another single value represents rock grains.

A technique known in the art for segmenting a gray-scale object is called "thresholding", where all pixels having a gray scale value below a selected threshold value (e.g., a gray scale value of 150 on a scale of 0 to 255) are identified as grains, while all other pixels are identified as pore space. The foregoing approach is often not satisfactory, however, because, due to numerical clutter in an unprocessed CT scan image, some pixels physically located inside a grain may have the gray level of the pore space and vice versa. In the invention, a type of image segmentation known as "region growing" can be used. Region growing may be described as follows. Consider a 2D section of a CT scan image made of a porous rock formation such as sandstone, which has primarily quartz rock grains. A substantial number of "seeds" (each seed consists of one or more pixels having a similar pixel gray scale level, e.g., 250±5) is placed within the image. All pixels within a seed are assigned the same gray scale level which may be an average (e.g., arithmetic) of the gray levels of all the pixels within the seed. The seeds in the image frame do not overlap spatially. Next, two or more adjacent seeds are merged and are identified as a "region" if the gray scale levels of the adjacent seeds have gray scale values within a selected difference threshold of each other. Each identified region is assigned a uniform (fixed) gray level, which can be a weighted average of the gray scale values of all the seeds that have been merged into the identified region. The foregoing process continues for all regions thus formed in the image frame. As a result, the unprocessed CT image is transformed into internally uniform regions plus unclassified pixels that were not assigned to any of the identified regions (because such pixels included gray scale values outside the allocation threshold criteria). Each of such unclassified pixels can be assigned to an adjacent region with the closest gray scale level. If the resulting number of regions is greater than two, however, the foregoing method simply fails to allocate the CT image correctly into grains and pores.

To address the foregoing problem with extending ("growing") seeds into regions, in the invention, instead of using seeds having different gray scale values, only two classes of seeds are used: all pixels having a gray scale value below a selected initial limit for the gray scale level of rock grains (e.g., 60) are classified as rock grains; and all pixels in which the gray scale level is larger than a selected initial limit for pore spaces (e.g., 130) are classified as pore space. One simple way of specifying these initial limits is by selecting the gray scale levels corresponding to the peaks of a gray level histogram. In many subsurface formations, such a histogram will be bimodal, wherein one mode value will correspond to the gray scale level of pores, and another mode value will correspond to the gray scale level of rock grains.

The next element in image classification according to the invention is to grow each of the two initially formed seeds by allocating to such seeds all adjacent pixels having gray scale levels within a selected tolerance, e.g., 130–5 for pore spaces and 60+5 for rock grains. The foregoing process can continue by incrementally increasing the gray scale lower limit for rock grains and incrementally reducing the gray scale upper limit for pore spaces until the two limits meet. The result is that all pixels will be allocated to either pore space or to rock grains, thus providing a fully segmented image.

A possible advantage of the foregoing procedure is that instead of forming multiple regions, the foregoing technique grows only two distinctive regions from start to end, thus avoiding the situation where multiple distinctive regions appear and then have to be reclassified into either pores or grains. If the resulting segmented image appears noisy (cluttered), it can be smoothed by any of conventional filters.

A schematic outline of the foregoing procedure follows. First is to preprocess the original image using the median or 2D Gaussian kernel filter. The size of the filter is provided by the user and should depend on, among other factors, the quality of the image (level of noise). It should be noted that the image segmenting procedure that follows has been demonstrated to be sufficiently noise resistant as to make the preprocessing frequently unnecessary.

Next, two user-selected thresholds, $t_1$ and $t_2$, are selected to determine initial regions for pore space and rock grains, respectively. The initial thresholds may be selected, for example, by analysis of a histogram of the gray scale values in the CT image. For every pixel $p_i$ having a gray scale level represented by $B(p_i)$:

if $B(p_i) > t_1$ then $p_i$ is identified as pore space; and
if $B(p_i) < t_2$ then $p_i$ is identified as rock grain.

If there are two or more contiguous pixels in any subset of the image frame that are classified according to the threshold procedure above, such contiguous pixels may be referred to as "clusters." All of the pixels allocated as explained above then become the image seeds from which region growing proceeds.

Finally, for each pixel classified as a pore, its eight neighbors (spatially contiguous pixels) in the 2D image plane are interrogated. If any of the interrogated neighbor pixels is not already identified as pore or rock grain, and the gray scale level of such pixel is within a preselected tolerance level of (or initially selected different between) the gray scale level assigned to the "pore" seed (as in Step 2 above), the interrogated neighbor pixel is then classified as a pore and is allocated to the "pore" cluster.

The foregoing contiguous pixel interrogation is also performed for pixels classified as rock grain. Contiguous, previously unallocated pixels having gray scale level within a preselected tolerance of the gray scale level of the rock grain seed are allocated to the rock grain cluster.

The foregoing cluster allocation and region growing process continues for both pore space and rock grain until all the pixels in the 2D image frame are interrogated. If any of the pixels is not classified as pore space or rock grain, the foregoing tolerance value for each of the pore space and the rock grain may be increased by a selected increment (for example five gray scale numbers), and the contiguous pixel interrogation and classification may be repeated. The foregoing tolerance increase and repeated adjacent pixel interrogation may be repeated until all or substantially all the pixels in the 2D image frame are allocated to either rock grain or pore space.

The foregoing region growing procedure is then repeated for each 2D image frame in the 3D CT scan image. The result is a three dimensional characterization of the pore structure of the rock samples on which CT imaging has been performed.

Figure 2:
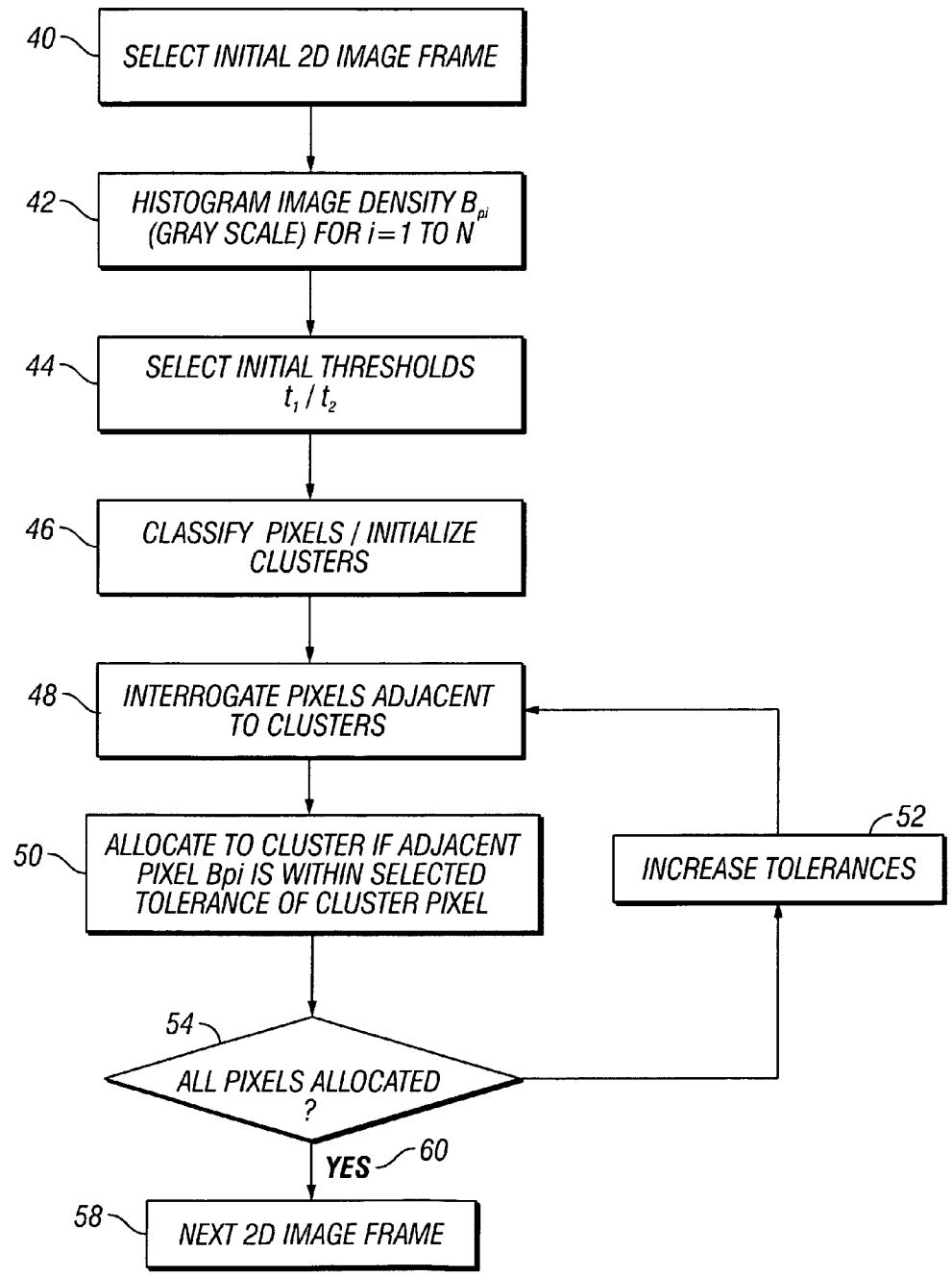
FIG. 2 shows a flow chart of an example process for CT image segmentation.

An example implementation of the above process for image segmentation is shown in a flow chart in FIG. 2. At 40, a 2D image frame of a CT scan image is selected. The image frame may be subjected to histogram analysis, at 42 to determine possible mode values of gray scale for pore spaces and for rock grains. At 44, the possible modes of the histogram may be used to set initial values for the image segmentation thresholds $t_1$ and $t_2$. At 46, using the initial segmentation thresholds, all pixels in the image frame are interrogated may be are allocated to pore space or to rock grains, depending on whether the gray scale value in each pixel exceeds the respective segmentation threshold. The allocated pixels are then segmented into seeds where two or more contiguous pixels are allocated to either pore space or rock grain. At 48, pixels adjacent to the each of the seeds are interrogated. Previously unallocated pixels having a gray scale value falling within an initially selected threshold difference (or tolerance) of the adjacent cluster pixel gray scale value are allocated to the seed at 50. At 54, the image frame is interrogated to determine if all or substantially all the image frame pixels have been allocated to either pore space or rock grain. At 54, the number of allocated pixels is counted and at 60 if all or substantially all the pixels in the image frame have been allocated, a new 2D image frame can be selected, at 58, and the above process repeated. Typically the next 2D image frame will be adjacent to the most recently analyzed 2D image frame. The above process can be repeated until all available 2D image frames have been analyzed. If all pixels in the image frame have not been allocated, at 52, the tolerance or difference threshold values used at 50 may be increased and the interrogation of pixels adjacent to the existing seeds can be repeated, at 48, and the remainder of the process can be repeated.

The result of the foregoing procedure is a segmented 3D image of the rock sample including image elements for rock grain and for pore space. Such image can be stored or displayed in a computer and can be used as input to one or more rock property characterization models.

Figure 3:
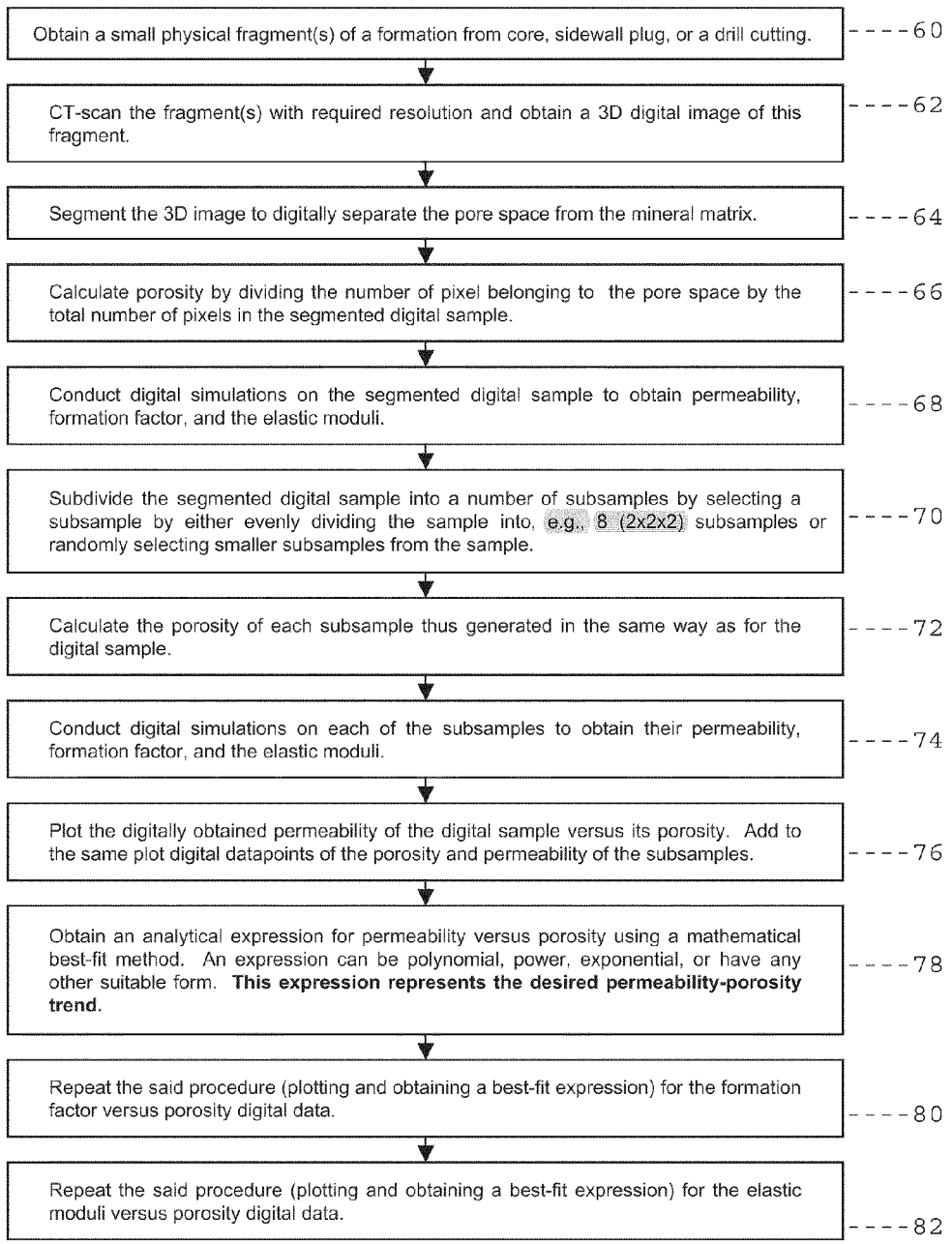
FIG. 3 shows a flow chart of an example analysis procedure according to the invention.

The foregoing implementation of image segmentation may prove advantageous when implementing analysis techniques according to the invention, which require a segmented image as input for further analysis. Such techniques may be explained as follows. In many cases, a relatively large range for each input parameter (e.g., porosity) can be obtained from a single sample of rock formation, for example drill cuttings (FIG. 1), sidewall cores, outcrop quarry or whole drill cores. Referring to FIG. 3, the sample of rock formation, obtained at 60, should be imaged, such as by CT-scanning, to obtain a high-resolution 3D image of the pore space and rock grains (matrix). The foregoing is shown at 62. Next, at 64, the image should be segmented to allocate image portions to the rock matrix and the pore space. Image segmentation may be performed as explained above with reference to FIG. 2.

By counting the pixels in the segmented image that are allocated to the pore space and dividing their number by the total number of pixels in the image, an estimate of the porosity $\phi$ may be obtained, at 66. Next, at 68, a numerical simulation of a physical experiment may be conducted on the sample image. Such numerical experiments and methods to conduct these experiments may include but are not limited to: (a) single-phase fluid flow using the Lattice-Boltzmann numerical method (LBM) to obtain the absolute permeability; (b) elastic deformation using the finite-element method (FEM) to obtain the imaged sample's elastic moduli and elastic-wave velocity; and (c) electrical current flow using FEM to obtain the imaged sample's electrical resistivity and formation factor. The foregoing procedure will produce a single data point, such as porosity/velocity, porosity/permeability, and/or porosity/formation factor, which is not sufficient to provide a rock physics transform for any of such data pairs.

To obtain a sufficient number of data points to establish relationships between porosity and other petrophysical parameters, the original segmented image volume may be subdivided into a selected number of sub-volumes, as shown at 70. Subdividing the image can be performed by dividing the original volume into a number of evenly spaced volumes or by randomly selecting a sufficient number of sub-volumes. One example is to divide a cubic image volume into sub-cubes. Examples of sub-cubes include dividing the original image volume into eight, twenty seven, sixty four or one hundred twenty five cubic sub-volumes. A value of porosity may be determined for each sub-volume, as shown at 72.

Because natural rock formations are heterogeneous at essentially all scales, it is often observed that even for a relatively homogeneous formation sample, such as Berea sandstone, the porosity and/or other attributes of sub-volumes typically includes a relatively large range of each petrophysical parameter of interest, and such range is typically sufficient to obtain a meaningful transform for each such parameter.

After subdividing the image volume and determining the porosity of each sub-volume, numerical simulation of any one or more petrophysical parameters of interest can be performed on each of the sub-volumes (just as performed on the entire image volume), at 72. The results may be plotted or otherwise allocated in the computed outputs (e.g., absolute permeability k) with respect to the input parameters (e.g., porosity $\phi$) at 76. The resulting data points often are sufficient in number to establish a relationship between them (i.e., a transform).

Next, the data points above are used, at 78, for the one or more modeled petrophysical parameters, to obtain a relationship such as a best-fit analytical expression between porosity and the petrophysical parameter(s). In a first example, the porosity may be related to permeability. The foregoing relationship determination may be repeated with respect to formation resistivity factor, at 80. The foregoing relationship determination may also be repeated for bulk, elastic and/or shear moduli, at 82.

In the present example, the Lattice-Boltzmann method can be used to numerically solve Navier-Stokes equations for flow simulation for permeability modeling. Such solution may be used to calculate permeability of simulated 3D volumes. The Lattice-Boltzmann method is a robust tool for flow simulation, particularly in media with complex pore geometry. See, for example. Ladd, *Numerical Simulations of Particulate Suspensions via a discretized Boltzmann Equation, Part* 1: *Theoretical Foundation*, J. Fluid Mech., v 271, 1994, pp. 285-309; Gunstensen et al., "*Lattice Boltzmann Model of Immiscible Fluids*, Phys. Rev. A., v. 43, no. 8, Apr. 15, 1991, pp. 4320-4327; Olsen et al., *Two-fluid Flow in Sedimentary Rock: Simulation, Transport and Complexity*, J. Fluid Mechanics, Vol. 341, 1997, pp. 343-370; and Gustensen et al., *Lattice-Boltzmann Studies of Immiscible Two-Phase Flow Through Porous Media,*" J. *of Geophysical Research*, V. 98, No. B4, Apr. 10, 1993, pp. 6431-6441).

The Lattice-Boltzmann method simulates fluid motion as collisions of imaginary particles, which are much larger than actual fluid molecules, but wherein such particles show almost the same behavior at a macroscopic scale. The algorithm used in the Lattice-Boltzmann method repeats collisions of these imaginary particles until steady state is reached, and provides a distribution of local mass flux. In accordance with the present invention, the Lattice-Boltzmann method is applied successfully for many pore structures, including cylindrical tubes, random densely packed spheres, and 3D rock samples digitized by CT scanning as explained above. See, for example, U.S. Pat. No. 6,516,080 issued to Nur.

It is also possible to estimate capillary pressure related flow characteristics from the pore structure determined using the 3D images processed as explained above. See, for example, U.S. Pat. No. 7,277,795 issued to Boitnott. Any or all of the foregoing estimated petrophysical properties and parameters may be stored and/or displayed in the computer (32 in FIG. 1).

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for estimating a relationship between physical properties of a porous material from a sample thereof, comprising:
    making a three dimensional tomographic image of the sample of the material;
    segmenting the image into pixels each representing pore space or mineral grain;
    subdividing the image into sub-volumes;
    estimating a porosity for each sub-volume from the image thereof;
    modeling at least one petrophysical parameter from the image of each sub-volume;
    determining a relationship between the porosity and the modeled petrophysical parameter using the estimated porosity and the modeled petrophysical parameter from a plurality of the sub volumes; and
    at least one of storing and displaying the relationship and the modeled petrophysical parameter, wherein the relationship is determined by statistical best fit.

2. The method of claim 1 wherein the tomographic image comprises a value of gray scale allocated to each of a plurality of pixels in the image.

3. The method of claim 2 wherein the segmenting comprises:
    (a) determining an initial gray scale threshold for each of pore space and rock grain;
    (b) allocating each pixel in the image to pore space or rock grain for each pixel meeting threshold criteria for each of the pore space and rock grain thresholds, respectively;
    (c) interrogating pixels adjacent to each seed;
    (d) allocating the interrogated adjacent pixels previously not allocated to a seed to the pore space seed or the rock grain seed based on threshold criteria; and
    (e) repeating (c) and (d) until substantially all pixels in the image are allocated to the rock grain or the pore space.

4. The method of claim 3 wherein the determining initial gray scale thresholds comprises histogram analysis of the tomographic image.

5. The method of claim 3 wherein the allocating interrogated adjacent pixels comprises determining a difference between a gray scale value and a gray scale value of the adjacent pixel in the seed, and allocating the interrogated pixel to the seed if the difference falls below a selected threshold.

6. The method of claim 5 further comprising:
    determining whether unallocated pixels exist in the image;
    increasing the selected difference threshold; and
    repeating the interrogating adjacent and allocating the interrogate pixels having gray scale values wherein the difference is below the increased difference threshold.

7. The method of claim 1 wherein the material comprises a rock formation.

8. The method of claim 7 wherein the at least one petrophysical parameter comprises permeability.

9. The method of claim 8 wherein permeability is estimated using the Lattice-Boltzmann approximation.

10. The method of claim 7 wherein the at least one petrophysical parameter comprises electrical resistivity formation factor.

11. The method of claim 7 wherein the at least one petrophysical parameter comprises at least one of elastic modulus, bulk modulus and shear modulus.

* * * * *